United States Patent [19]

Matzuk

[11] Patent Number: 4,671,292
[45] Date of Patent: Jun. 9, 1987

[54] CONCENTRIC BIOPSY PROBE

[75] Inventor: Terrance Matzuk, Verona, Pa.

[73] Assignee: Dymax Corporation, Pittsburgh, Pa.

[21] Appl. No.: 728,787

[22] Filed: Apr. 30, 1985

[51] Int. Cl.[4] ............................................. A61B 10/00
[52] U.S. Cl. ............................................... 128/660
[58] Field of Search ............... 128/660, 24 A; 73/609, 73/618–621

[56] References Cited

U.S. PATENT DOCUMENTS

| | | | |
|---|---|---|---|
| 4,092,867 | 6/1978 | Matzuk | 73/609 |
| 4,108,165 | 8/1978 | Kopp et al. | 128/660 |
| 4,330,874 | 5/1982 | Sorwick | 128/660 X |
| 4,346,717 | 8/1982 | Haerten | 128/660 |
| 4,398,540 | 8/1983 | Takemura et al. | 128/660 |
| 4,399,703 | 8/1983 | Matzuk | 73/621 |
| 4,402,324 | 9/1983 | Lindgren et al. | 128/660 |
| 4,479,388 | 10/1984 | Matzuk | 73/634 |
| 4,527,569 | 7/1985 | Kolb | 128/660 |
| 4,542,747 | 9/1985 | Zurinski et al. | 128/660 |

FOREIGN PATENT DOCUMENTS 2907504 9/1980 Fed. Rep. of Germany ...... 128/660
2124057 2/1984 United Kingdom ................ 128/660

Primary Examiner—Kyle L. Howell
Assistant Examiner—Francis J. Jaworski
Attorney, Agent, or Firm—Weingarten, Schurgin, Gagnebin & Hayes

[57] ABSTRACT

An ultrasound imaging probe suitable for concentric on-axis biopsy procedures. The probe according to the present invention includes an aperture through which a biopsy needle is inserted to sample a target tissue previously located by the ultrasound probe. In operation, the ultrasonic probe is first positioned on the subject over a target tissue. A cursor is moved to visually overlap the target tissue within the subject, and the depth is indicated on a corresponding display. A biopsy needle is selected and adjusted to extend to the indicated depth when inserted through the ultrasonic probe and transducer aperture into the subject. Thus the apparatus according to the present invention provides for the improved biopsy procedures through the use of a probe having a needle entranced through the source aperture, used for imaging, thus minimizing risk and error arising from conventional off-axis needle entrances.

10 Claims, 7 Drawing Figures

CONCENTRIC BIOPSY PROBE

FIELD OF THE INVENTION

The present invention relates to ultrasonic scanners, and in particular to ultrasonic scanning apparatus for use with a biopsy needle for accurate positioning thereof.

BACKGROUND OF THE INVENTION

Accurate biopsy procedures require the use of accurate position determination of the site relative to the surface of the subject. Previous procedures have included the use of multiple x-rays or fluoroscopic scans, and careful determination to locate the site on the surface of a patient through which a biopsy probe could be inserted. Since significant time may elapse between the location of the site and the actual biopsy procedure, the accuracy of the process can be compromised due to patient motion and errors in the administration of the procedure.

DETAILED DESCRIPTION OF THE INVENTION

The probe according to the present invention is structurally configured to operate as an ultrasound imaging probe suitable for on-axis concentric biopsy procedures. The design according to the present invention includes a closed-loop continuous position feedback servo system. The differential coil position-sensor principle of the oscillating mirror drive system (OMDS) (U.S. Pat. No. 4,479,388), incorporated by reference, is employed in a novel fashion to make position sensing feasible where otherwise difficult, owing to the obstruction caused by the central axis opening.

Figure 1:
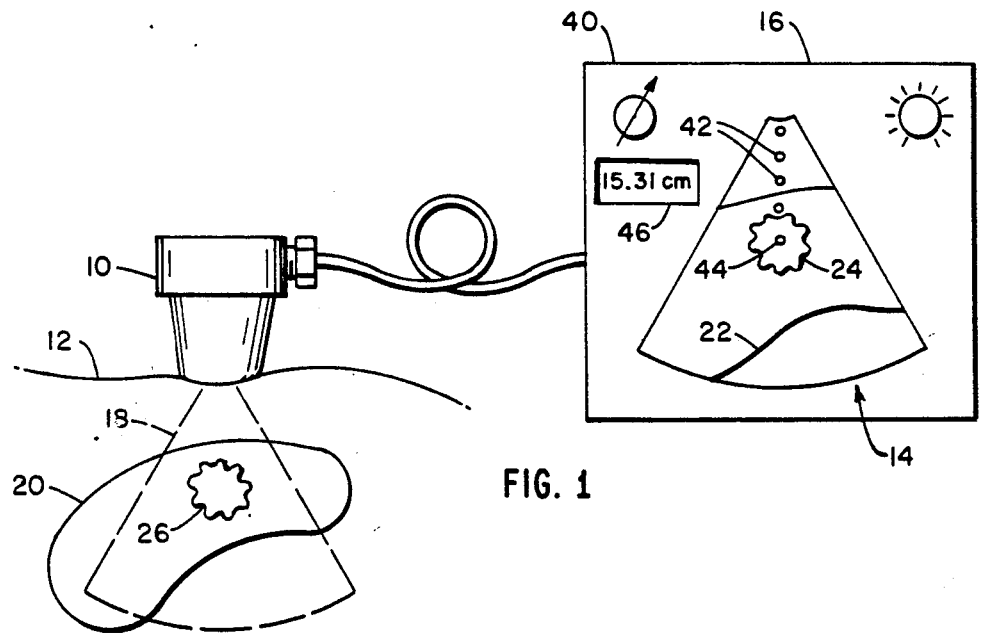
Figure 2:
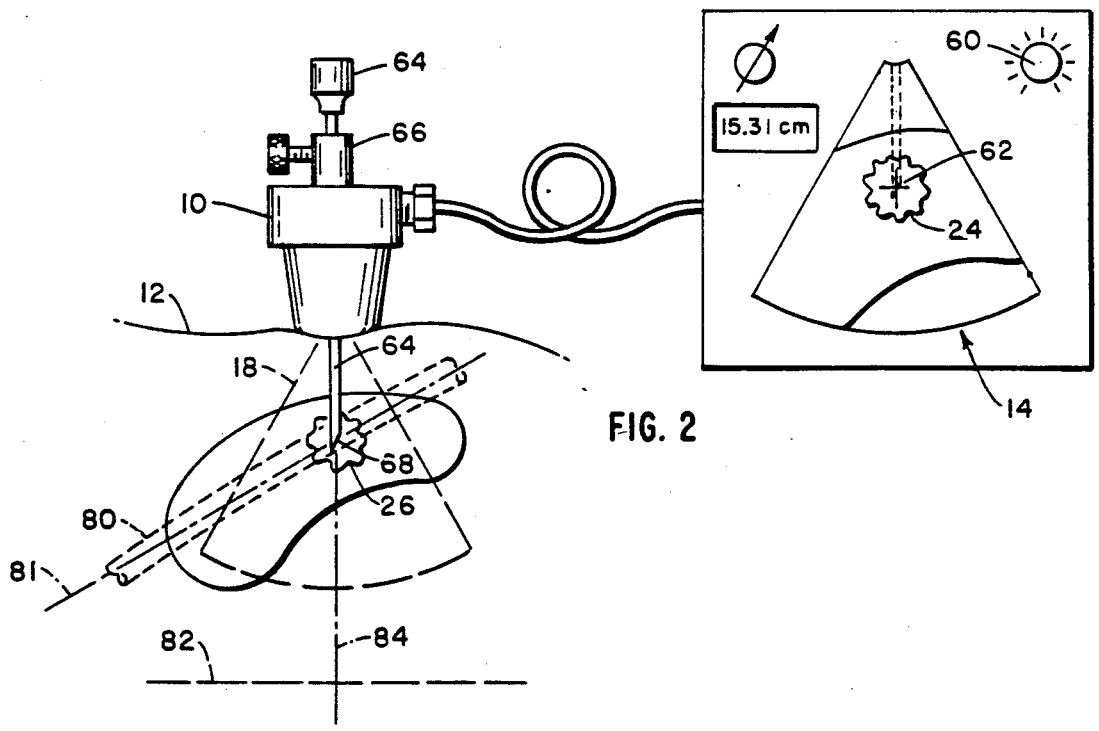

FIGS. 1 and 2 show the use of the probe according to the present invention.

Referring to FIG. 1, the probe 10 is placed upon the subject body 12 to obtain an image 14 on display console 16 corresponding to the sector cross-sectional scan 18. An organ 20 is partially or entirely visualized 22 including an image 24 of a lesion (e.g., tumor) 26 within organ 20. Initially the sector scan 18 is set to cover a large angle (e.g., 50°-60°) and a deep field of view (e.g., 15 cm in depth) to visualize the entire ogran. When lesion 26 is identified, the invasive radiologist (user) elects to reduce the field of view (e.g., 8 cm) and angle (e.g., 30°) to "zoom in" upon the lesion 26 of interest. Control 40 is manipulated tactually to cause central scrolling cursor 42 to descend vertically until the first dot 44 drops to the correct depth of lesion 26. The user maintains the lesion's image 24 laterally in the center of the scan.

A numerical depth display 46 indicates the depth of lesion 26 in centimeters according to the location of the first cursor dot 44. The probe 10 is removed from body 12. A biopsy needle (64 of FIG. 2) is fitted with an adjustable stop 66 which is set to the sum of the reading in centimeters of numerical display 46 and the probe height in centimeters. Referring to FIG. 2, probe 10 is again placed upon body 12 and the image 24 of lesion 26 is centered in the sector display 14, repositioning the first dot over the image 24 of the lesion 26 (of FIG. 1). Tactual depression of control 60 causes scrolling cursor 42 to disappear and cross 62 to appear at the previous location of first dot 44 (of FIG. 1). At this time, the needle 64 with correctly attached stop 66 is pushed through an opening beginning in the rear structure of probe 10 and continues into body 12 until tip 68 of needle 64 arrives within the center of lesion 26. The corresponding events on display console 16 depict the image of tip 68 of needle 64 travelling downward until this image coincides with cross 62. At this time the user is free to take a tissue sample, aspirate liquid (if lesion is cystic), or to inject contrast media (e.g., Renographin). The needle 64 may be retracted without removing probe 10 from body 12 in case the user decides to see the effect (reduction or dilatation of size of lesion 26) as a result of the user's invasive procedure.

In the event that target 26 is no longer a lesion but a blood vessel 80 along an axis 81 inclined away from the perpendicular (line 82) to the probe axis, the probe 10 can be used in the standard Doppler mode. The continuously moving sector scanning action of probe 10 is stopped under servo control to a selected ray (e.g. central ray 84) and the Doppler blood flow spectrum is confirmed prior to the application of the method previously described. Usage of Doppler techniques aids in the classification of the blood vessel 80 (arterial or venous flow, or no flow) prior to invasion with needle 64. Invasion of vessel 80 may be of interest, for example, in order to introduce a catheter through the lumen of the vessel 80. Frequently the localization of a blood vessel may be very difficult without the aid of Doppler guidance or sector image. The method described in reference to FIGS. 1 and 2 may also be applicable to safe removal of pleural fluid. This method is further applicable to biopsy of brain tumors and is preferable to existing methods because the tumor can be visualized and biopsyed through a single standard burr hole in the skull without the need to raise a flap in the cranial vault.

Figure 3:
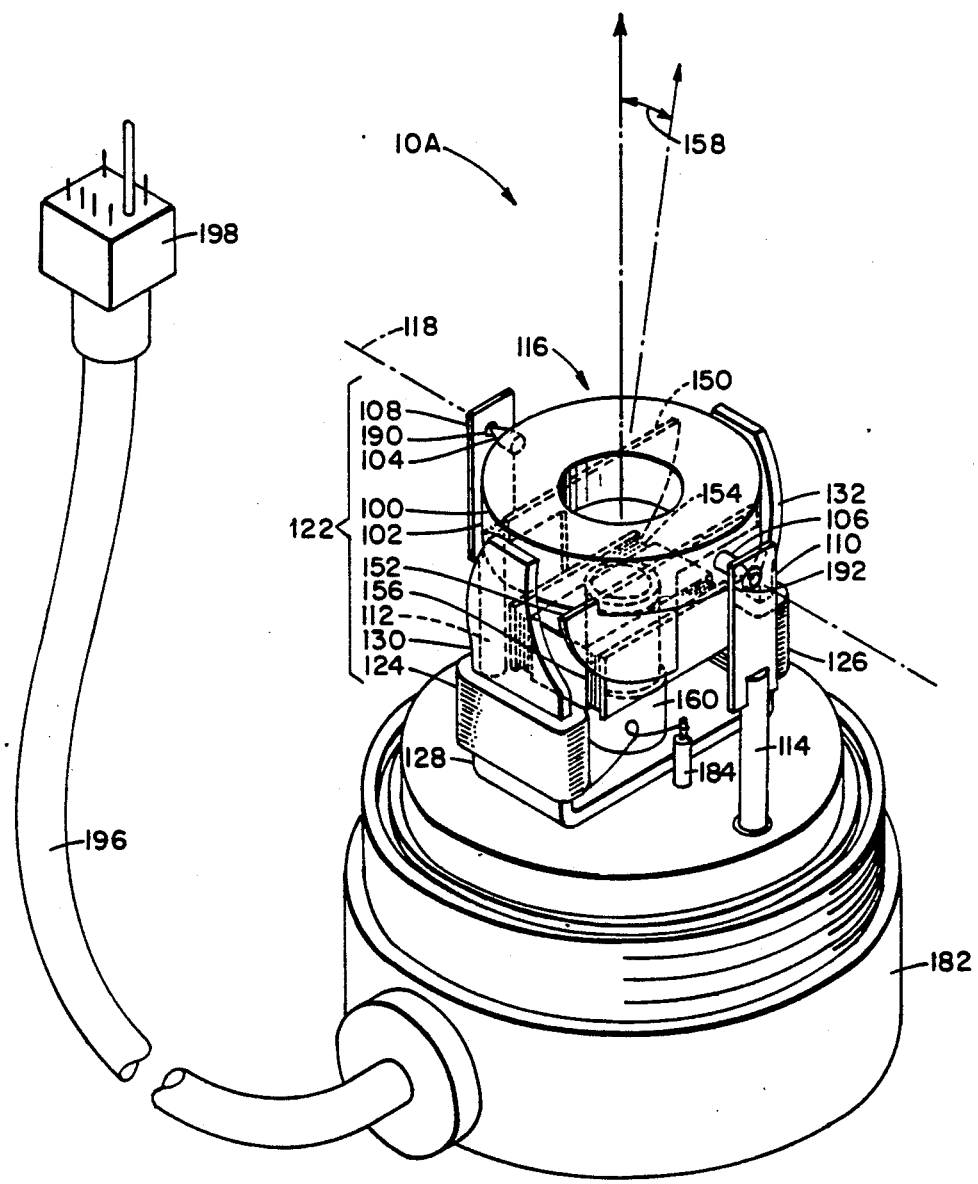

FIG. 3 depicts the biopsy probe 10A, minus the cover of probe 10 of FIGS. 1 and 2, facing upward in a perspective view. An annular focussed ultrasound crystal 100 is mounted on a machinable permanent magnet 102 which serves as part of an electromagnetic drive, a structural support, and as an acoustical damper that prevents acoustical energy from propagating backwards inside the probe and improves the transient response (axial resolution) of crystal 100. Bearing pins 104, 106 engage embossed leaf springs 108, 110 attached to supports 112, 114. Rotor assembly 116, including crystal 100 and permanent magnet 102, rotates on bearing axis 118 through a preprogrammed arc, typically within the range of 0–60 degrees. The acoustical beam from the crystal 100 emanates along axis 120 perpendicular to the face plane of crystal 100. The entire mechanism 122 operates in oil (562) contained by the cover (500 in FIG. 6). The purpose of the oil is to couple the acoustical beam 120 towards the outside surface of the cover. Currents in coils 124, 126 create electromagnetic fields in the U-shaped pole piece structure 128.

Position sensing metal vanes 150, 152 partially cover coils 154, 156 to a degree dependent upon the angle 158 of rotor assembly 116, thereby modulating both the inductance and quality factor of coils 154, 156 in a differential manner so that, connected to suitable circuitry, a reading of angle 158 may be taken continuously. Not visible in FIG. 3 is a hole going completely through axis 120 and through needle shield 160 whose function it is to prevent needle entry from distorting the position reading from coils 154, 156. Coils 154, 156 are excited by modest levels of radio-frequency currents at 460 KHz, well below the frequencey range (5 MHz) of the pulse-echo signal to prevent interference. Signals to and from crystal 100 are connected through members 108, 112, 110, 114 to the lower housing 182 and cable 196. It is desirable to electrically ground the needle shield 160, vanes 150, 152, the front surface of crystal 100 and the upper surface 180 of lower housing 182 to eliminate external interferences.

Electrical connections are made through liquid-tight bushings (e.g., 184) and liquid-sealed fittings along the lower portion of members 112, 114. Springs 108, 110 contain bearing pins 104, 106 within alignment through indented embossed depressions 190, 192. Bearing pins 104, 106 are compressed between springs 108, 110 to insure reliable electrical contact under oil. It is important that the metals of pins 104, 106 be dissimilar from the metals of springs 108, 110 to insure a non-crazing polishing action that increases the surface area of contact during scanning. This increase in surface area has the effect of reducing the peak current density during pulsing of crystal 100 and has the effect of reducing both the average value and the fluctuation of the average value of the bearing resistance during the listening periods. This is important because low bearing impedance conditions permit one to place the customary shunt inductor 98 (associated with crystal 100) *outside* rotor assembly 116 in order to reduce the moment of inertia of assembly 116, which has the effect of minimizing motor power. This in turn has the effect of minimizing probe temperature rise which minimizes liquid expansion (greater than case expansion), which makes simple seals of small dimensions possible. The liquid must be non-oxidizing to enhance the polishing action of bearings 104, 106, 108, 110. The occasional minute arcing present during the start-up phase of probe life will be self-quenching when the oil and metals are properly selected, thereby insuring reliable commutation. With the proper choice of materials and liquids such as the oil 562, an extremely simple pivot bearing design is mechanically sturdy and reliable in excess of 1000 hours. Cable 196 and plug 198 make the obvious connections to the display console (16 of FIGS. 1 and 2).

Figure 4:
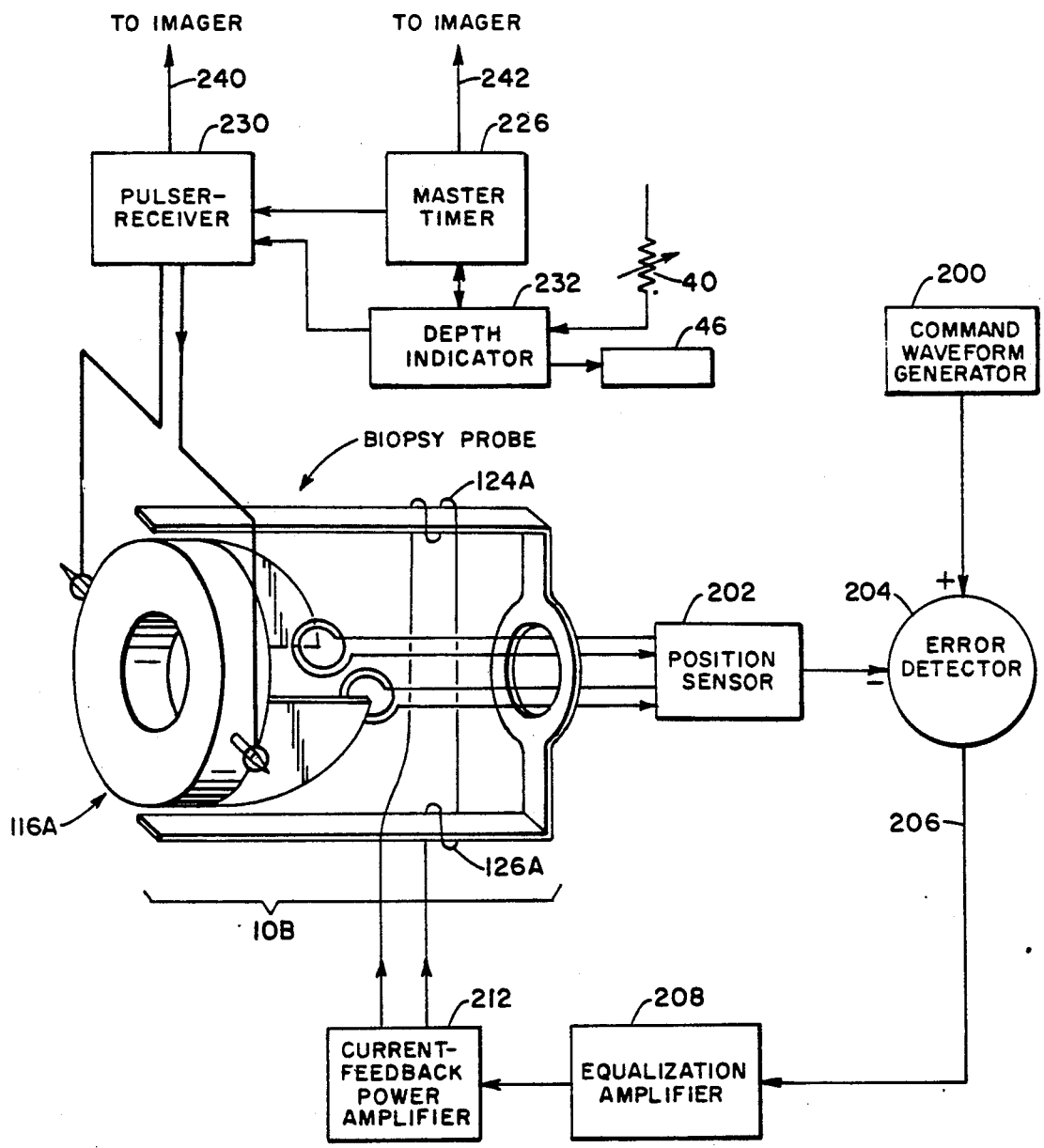

FIG. 4 shows the probe 10B connected to a continuous position feedback servo probe control system shown generally in U.S. Pat. No. 4,092,867. A command waveform generator 200 produces triangular scanning waveform or DC stop angle signal voltages which are subtracted from the sensor position 202 output signal at error detector 204. The error signals 206 are amplified and twice differentiated within equalization amplifier 208 and the output 210 is applied to current-feedback current amplifier 212 to effect an optimally stabilized servo system. Amplifier 212 powers the drive coils 124A, 126A of probe 10A to effect the oscillating motion of rotor assembly 116A. Meanwhile the master timer 226 fires the pulser and sets up the ramp functions in the receive 230 and video output signals 240 entertain the display console 16 along with sync signals 242.

The scrolling cursor 44 is generated by scroll generator 232 having control 40 and depth indicator 46 connected thereto. The cursors 42 and 44 are gated to coincide with the beam scan centrally located within the scan 18. Since each scan indicates depth according to the time of the ultrasound reflection signals, the corresponding cursors 42 and 44 are produced by gating a signal (or series of pulses for "dotted" cursor, shown) during a corresponding period of selected scan. The depth is then determined according to the time of the last cursor 46 and displayed (on 46).

Figure 5:
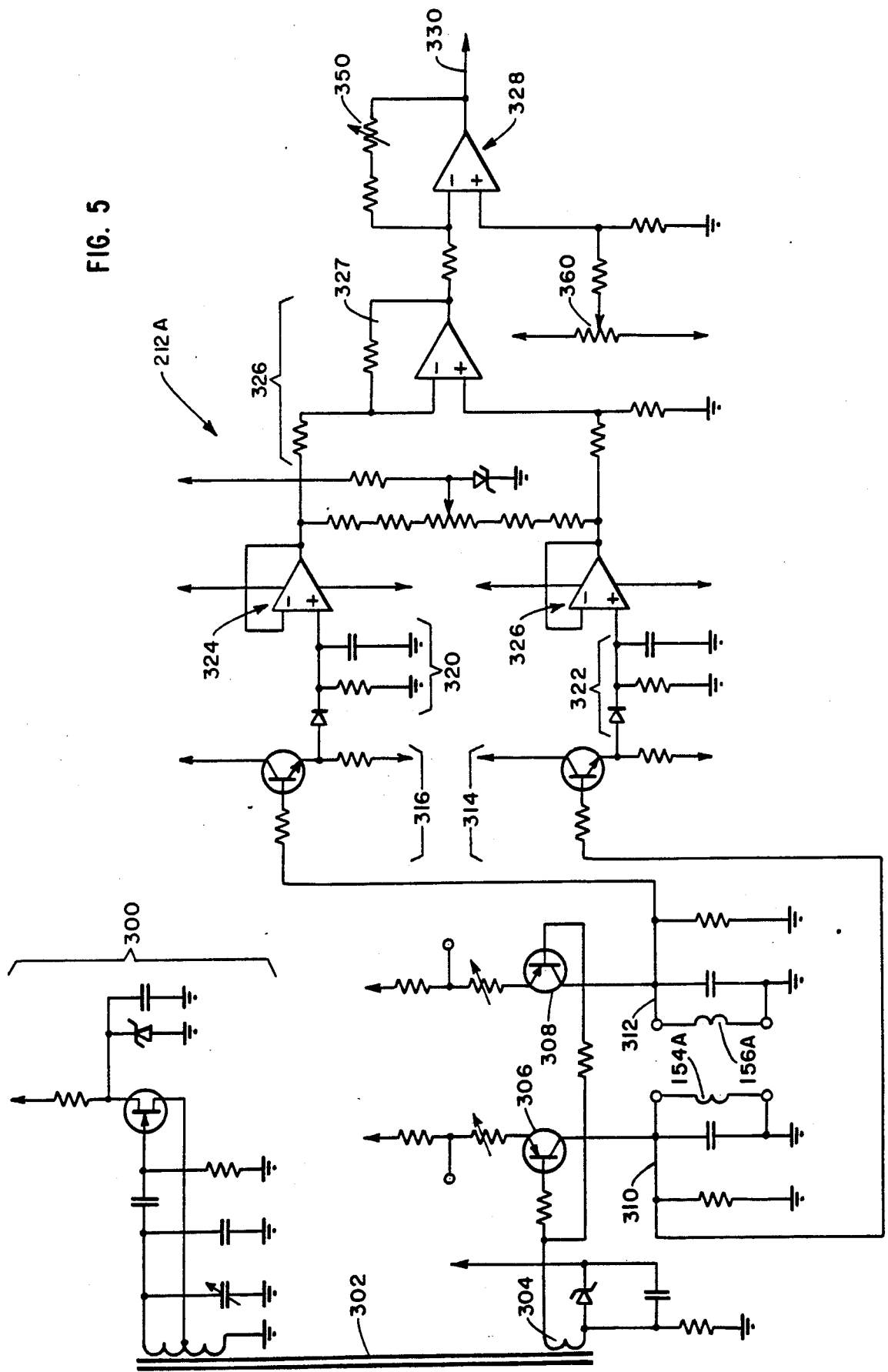

The position sensor 202 comprises the circuit diagram 202A, shown in FIG. 5, is the position sensor circuit. The circuit 202A provides an error signal output at 320 in response to signals developed by the differential coils position sensor assembly 150, 152, 154, 156 (of FIG. 3). Referring to FIG. 5, a Hartley oscillator 300 is magnetically coupled 302 to a low-impedance winding 304 that powers two constant-current R.F. sources 306, 308 at 460 KHz to drive position sensing coils 154A, 156A, corresponding to coils 154 and 156 inside probe 10 of FIG. 3. The differentially varying R.F. envelopes developed at points 310, 312 are amplified at 314, 316 and envelope detected at 318 and 320. The signals are buffered at 322 and 324, and differentially amplified at 326. The output at 327 is again amplified at 328, and the output signal at 330 is fed to the error detector (204 of FIG. 4). Referring to FIG. 5, the gain calibration 350 and offset trimming 360 adjustments are provided.

Figure 6:
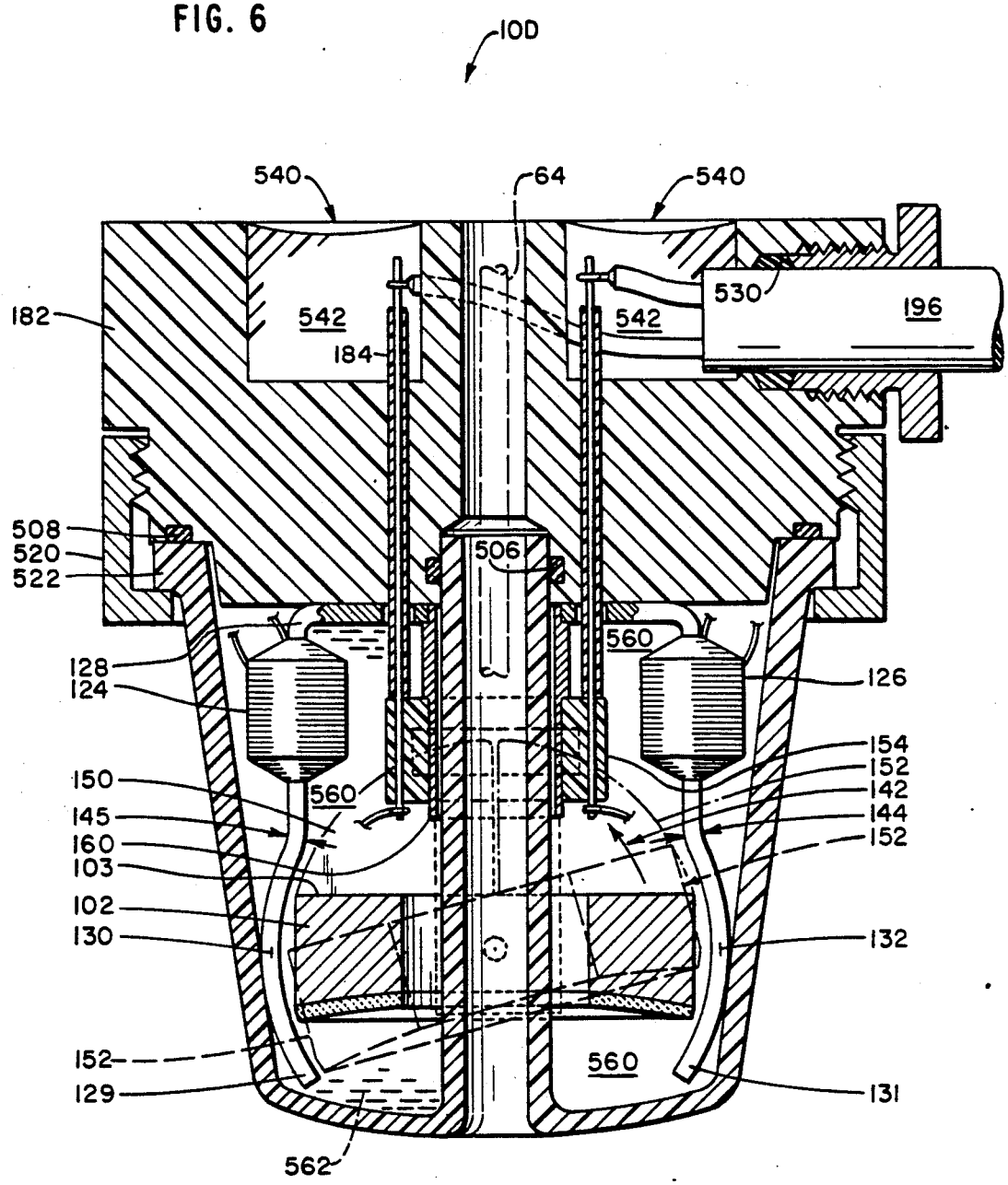

FIG. 6 summarizes the probe 10D in cross section. Of particular interest is the cross section 500 of the cover featuring an annular design. The needle hole beginning at 502 continues through the lower housing 182 and exists through opening 504. An internal O-ring 506 effects the liquid 562 in the vicinity of the needle hole, and an external O-ring 508 effects the seal at the outer flange of cover 500. Retaining ring 520 axially compresses flange 522 of cover 500 to insure sealing action of O-ring 508. O-ring 530 seals cable 196 under compression of locking nut 532. Liquid-tight seals of electrical members 184 are accomplished with epoxy encasement 542 in annular region 540.

The cross section of the needle shield 160 is shown. Shield 160 prevents magnetic fields from coil 154 from being distorted by entry of the needle 64. The only time-varying modification of magnetic fields of coil 154 are due to the partial occluding action of position-sensing vane 150. The liquid 562 is contained in regions 560.

The pole extensions 130, 132 are shaped to optimize the linearity of the scanning waveform, the drive efficiency, and the ability for the rotor to passively stop in the center of the sector scan. Fields terminating in specially shaped pole piece 128 (of FIGS. 6 and 7) extensions 130, 132 interact with magnet 102 to produce torques and rotational accelerations that impart oscillating motion to assembly 116. The shape of extensions 130, 132 is important, as it determines (1) the ability for the rotor assembly 116 to remain passively (without energization of coils 124 and 126) perpendicular to the on-axis 120 position, (2) the high overall drive efficiency, (3) the effect of a "magnetic return spring" action at the extremes 144 of the sector scan; and (4) providing the right clearance to make the position sensor feasible and to make the case feasible (for a standard 18-mm cranial burr hole).

Figure 7:
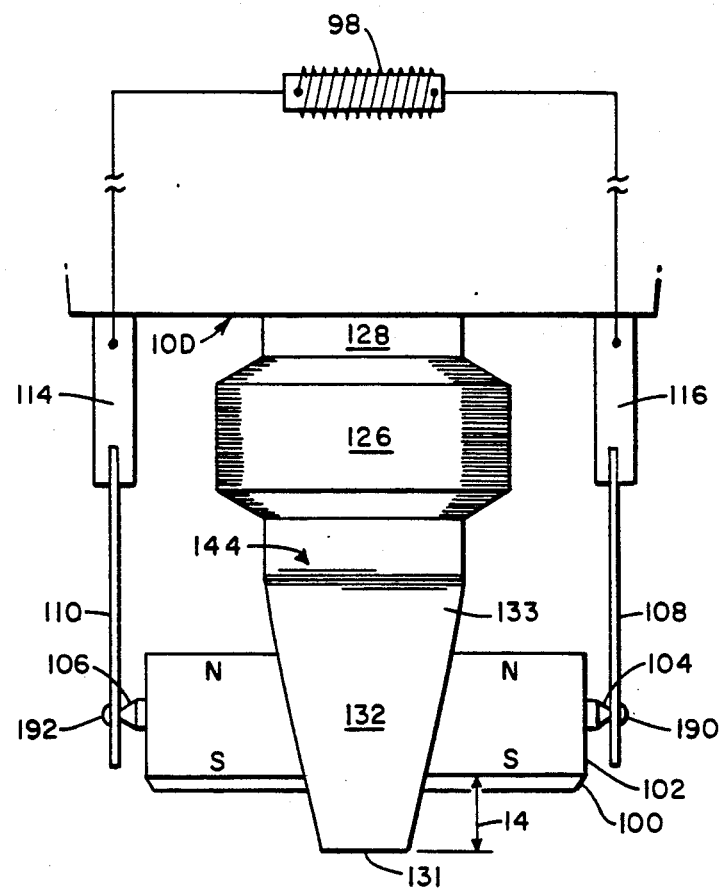

In particular, as shown in FIG. 7, the pole piece extension 132, as well as the opposite pole piece extension 130 (not shown in FIG. 7) are tapered from the coil end 133 to the tip 131, which when in combination with the rotor 100 magnet 102 having north (N) and sourth (S) poles on opposite surfaces, provide a uniform (constant) restoration force toward a neutral position, (shown in FIGS. 3 and 4). The exact taper is determined according to the magnet parameters and pole spacing and other dimensions. The electromagnetic drive means may also employ pole pieces shaped as the poles according to the probe in U.S. Pat. No. 4,399,703, incorporated by reference.

Moreover, as shown in FIG. 6, the pole pieces 130, 132 are curved to provide a uniform, minimum spacing with the rotor 100 throughout the arc of the pole pieces 130, 132. The tips of the pole pieces 129 and 131 extend forward of the magnet 102 (with neutral or quiescent position shown in solid), preferably one-half of the magnet 102 thickness. The pole piece extensions 130, 132 curve circumferentially about the path of the rotor 100 until they depart at 144 to form straight sections on which to receive the magnetic coils 124, 126. As the rear surface 103 of the magnet 102 continues to move (from neutral) beyond 142 the pole location 144 (or 145 for pole piece 130), the increased reluctance causes a sharp increase in force, introducing a sharp restoration force to "kick" the rotor in the opposite direction. Therefore, the combination of the tapered pole pieces 130, 132 and the formation of the pole pieces at 144, 145 produce a magnetic drive having a predictable neutral position without an additional spring constant, and an inherent rotor motion reversing effect.

Conventional sterile techniques (such as draping) and standard ultrasonic techniques (such as establishing acoustical coupling with Surgilube) have not been included in the description of this method.

What is claimed is:

1. An ultrasonic probe for use with a biopsy needle, comprising:
    mechanical scanning means for providing an ultrasonic beam movable through an angle describing a path according to an energization signal, said means including an aperture therein to permit said biopsy needle to be aligned with its axis coincident with the axis of a beam in the path and including means to provide a beam coincident with said biopsy needle axis upon removal of said energization signal while said needle is placed within said biopsy probe; and
    means for guiding said biopsy needle through said aperture to intercept said path mounted on said ultrasonic probe for providing accurate and measurable movement of said biopsy needle therethrough.

2. The ultrasonic probe of claim 1, wherein
said means for providing an ultrasonic beam is operative to further provide receipt for ultrasonic signals along said beam.

3. The ultrasonic probe of claim 2, further including display means receiving the received ultrasonic signals providing a two-dimensional visual image of the received ultrasonic signals along a beam angle axis and a depth of reflection axis.

4. The ultrasonic probe of claim 3, further including display cursor means for providing a visual indication of a selected depth of a selected beam angle; and
means to provide a numeric value corresponding to said selected cursor depth in response to the received ultrasonic signals.

5. The ultrasonic probe of claim 1, wherein
said means for providing a moving ultrasonic beam comprises an annular means.

6. The ultrasonic probe of claim 1, wherein
said means for providing a moving ultrasonic beam includes an ultrasonic transducer having a radiating surface.

7. The ultrasonic probe of claim 1, wherein
said means for providing a moving ultrasonic beam includes a motor means and a motor drive means, wherein said beam is directed through said path according to a position signal provided to said motor drive means.

8. The ultrasonic probe of claim 7, wherein
said servo drive means includes differential inductive position sensing means.

9. The ultrasonic probe of claim 7, wherein
said servo drive means includes a magnetic drive means comprising a permanent magnet connected to said means for providing a moving ultrasonic beam and a drive electromagnet providing a varying magnetic field according to said position signal.

10. A biopsy probe, comprising:
    a fluid filled housing having an aperture therein for receiving a biopsy needle therethrough;
    means for guiding said biopsy needle through said aperture in said fluid filled housing along a first axis;
    a permanent magnet having oppositely disposed magnetic poles;
    pivot means to movably retain said permanent magnet about a second axis in said fluid-filled housing, comprising a plurality of pivot contacts providing electrical connection through said second axis;
    an ultrasound crystal retained by said permanent magnet and connected to said pivot contacts, said ultrasound crystal having an aperture therein and providing an ultrasound beam along a third axis orthogonal to said second axis and describing a sector path to selectively include said first axis;
    an inductor electrically connected to said pivot contacts and mechanically separate from said ultrasound crystal; and
    an apertured electromagnet retained in said housing having tapered end poles disposed in opposition for providing a selected magnetic field therebetween and being mounted proximal to said permanent magnet poles wherein said tapered poles extend beyond said magnet and provide a restoration force path relative to said permanent magnet to position said ultrasound beam to coincide with said biopsy needle when said electromagnet is unenergized.

* * * * *